United States Patent
Hetting

(10) Patent No.: US 9,675,764 B2
(45) Date of Patent: Jun. 13, 2017

(54) PISTON FOR USE A SYRINGE WITH SPECIFIC DIMENSIONAL RATIO OF A SEALING STRUCTURE

(71) Applicant: INJECTO A/S, Hellerup (DK)

(72) Inventor: Mikkel Hetting, Klampenborg (DK)

(73) Assignee: INJECTO A/S, Hellerup (DK)

( * ) Notice: Subject to any disclaimer, the term of this patent is extended or adjusted under 35 U.S.C. 154(b) by 0 days.

(21) Appl. No.: 14/895,272

(22) PCT Filed: Jun. 4, 2014

(86) PCT No.: PCT/DK2014/050161
§ 371 (c)(1),
(2) Date: Dec. 2, 2015

(87) PCT Pub. No.: WO2014/194918
PCT Pub. Date: Dec. 11, 2014

(65) Prior Publication Data
US 2016/0129197 A1    May 12, 2016

(30) Foreign Application Priority Data

Jun. 5, 2013 (DK) ................... 2013 00342
Aug. 6, 2013 (DK) ................... 2013 70433

(51) Int. Cl.
*A61M 5/315* (2006.01)
*A61M 5/32* (2006.01)
(Continued)

(52) U.S. Cl.
CPC ...... *A61M 5/3202* (2013.01); *A61M 5/31513* (2013.01); *A61M 5/502* (2013.01); *A61M 2005/3109* (2013.01)

(58) Field of Classification Search
CPC ............ A61M 5/31513; A61M 5/3202; A61M 2005/3131; A61M 5/3134
See application file for complete search history.

(56) References Cited

U.S. PATENT DOCUMENTS 2,551,339 A * 5/1951 Ryan ................ A61M 5/28
                                          604/193
2,591,046 A * 4/1952 Brown ............... A61M 5/284
                                          222/136
(Continued)

FOREIGN PATENT DOCUMENTS

DE      2001366 U1     9/2000
EP      0047442 A1     3/1982
(Continued)

OTHER PUBLICATIONS

Search Report issued Mar. 12, 2014 by the Danish Patent and Trademark Office for Danish Patent Application No. PA 2013 70433.

(Continued)

*Primary Examiner* — Kevin C Sirmons
*Assistant Examiner* — Deanna K Hall
(74) *Attorney, Agent, or Firm* — Holland & Hart LLP

(57) ABSTRACT

A piston for use in an injector comprising a cylinder having a longitudinal axis and an inner wall, which piston has a deformable sealing element with a convex surface, which deformable sealing element when the piston is inserted in the cylinder abuts the inner wall of the cylinder at an abutting interface and seals an annular gap between the piston and the inner wall of the cylinder. The abutting interface and the deformable sealing element have axial dimensions parallel with the longitudinal axis. The ratio between the axial dimension of the abutting interface and the axial dimension of the deformable sealing element is in the range between 0.01 and 0.2. In another aspect, an injector includes the piston and is used in a disposable syringe of the piston. The piston can prevent refilling of a syringe.

17 Claims, 8 Drawing Sheets

(51) Int. Cl.
*A61M 5/50* (2006.01)
*A61M 5/31* (2006.01)

(56) References Cited

U.S. PATENT DOCUMENTS

| | | |
|---|---|---|
| 3,545,607 A | 12/1970 | Keller |
| 4,252,118 A | 2/1981 | Richard et al. |
| 4,317,446 A * | 3/1982 | Ambrosio ............ A61M 5/315 604/193 |
| 4,430,082 A | 2/1984 | Schwabacher |
| 5,158,549 A | 10/1992 | McCarthy |
| 5,795,337 A | 8/1998 | Grimard |
| 6,511,459 B1 | 1/2003 | Fago |
| 2001/0056264 A1 | 12/2001 | Sayama et al. |
| 2002/0032413 A1 | 3/2002 | Koch et al. |

FOREIGN PATENT DOCUMENTS

| | | |
|---|---|---|
| FR | 1600637 A | 7/1970 |
| WO | 0040280 A2 | 7/2000 |
| WO | 0232485 A1 | 4/2002 |
| WO | 2004033018 A1 | 4/2004 |
| WO | 2004075958 A2 | 9/2004 |
| WO | 2004078243 A2 | 9/2004 |
| WO | 2008064283 A2 | 5/2008 |
| WO | 2009128265 A1 | 10/2009 |

OTHER PUBLICATIONS

Search Report issued May 8, 2015 by the Danish Patent and Trademark Office for Danish Patent Application No. PA 2014 70805.

PCT International Search Report issued Nov. 18, 2014 by the European Patent Office for PCT International Patent Application No. PCT/DK2014/050161.

* cited by examiner

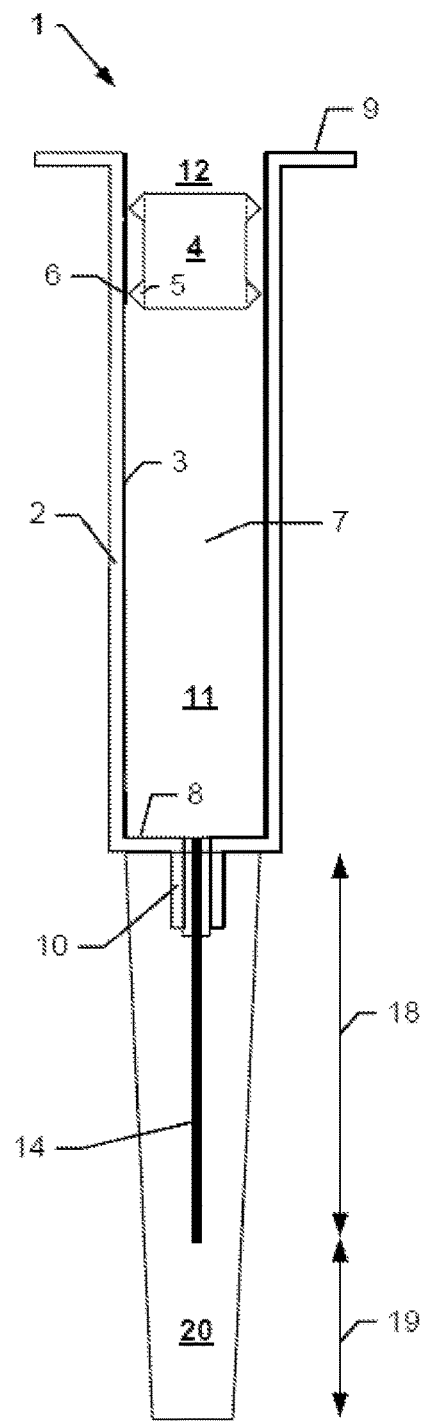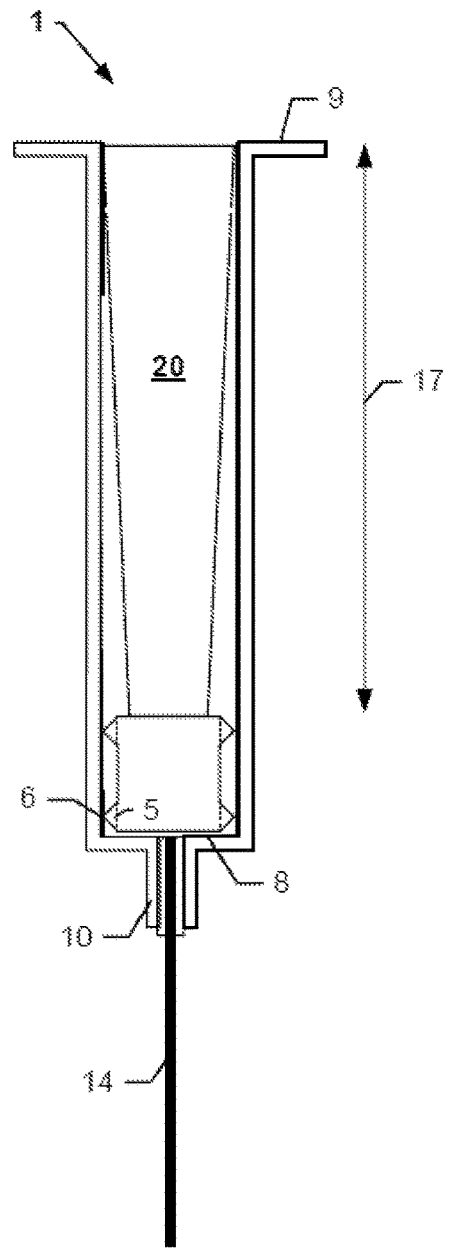
Fig. 5a                    Fig. 5b

PISTON FOR USE A SYRINGE WITH SPECIFIC DIMENSIONAL RATIO OF A SEALING STRUCTURE

TECHNICAL FIELD

The present invention relates to a piston for use in an injector comprising a cylinder with the piston having a deformable sealing element with a convex surface, which deformable sealing element abuts the inner wall of the cylinder at an abutting interface and seals an annular gap between the piston and the inner wall of the cylinder. The invention also relates to the injector and a piston rod for the injector. The injector of the invention is suited for delivery of a pharmaceutical composition, such as a vaccine.

BACKGROUND OF THE INVENTION

Known disposable syringes are in many cases constructed so that they can be reused, despite that they are intended only for a single use. One can refill the syringe by a pull of a traditional plunger, which through its connection with a piston refills a cylindrical barrel for secondary injection. The construction of a syringe without any measures to prevent reuse is typically simpler since it does not require such additional measures. In many cases the possibility to reuse a disposable syringe is of no concern. However, due to lack of necessary medical equipment, it has become common in especially poor developing countries to reuse disposable syringes, which only have been scanty cleaned and sterilised due to inadequate sanitary and hygienic conditions.

Examples of disposable syringes are provided in U.S. Pat. No. 5,795,337, WO 2004/078243, WO 2004/075958, WO 2004/033018, U.S. Pat. No. 4,252,118, U.S. Pat. No. 5,158,549, and WO 2002/32485. Further examples of syringes are provided in U.S. Pat. No. 4,430,082, EP 0047442, FR 1600637 and U.S. Pat. No. 3,545,607.

There is however a certain area within injections where the user will go to great lengths to manipulate a disposable syringe for reuse. In connection with vaccination campaigns carried out in poor third world countries, it is rather normal to apply pressure through the needle, which pressure is often created manually by use of a larger standard syringe, which pressure refills the syringe with vaccine through the glass vial for a secondary injection.

Undesired reutilisation is furthermore very widespread among drug abusers where one or more persons unhesitatingly utilise the same syringe and needle without prior sterilisation.

Such reuse of disposable syringes often results in human beings being infected with life-threatening diseases both in hospitals, clinics and vaccination sites all over the world and contribute to the spreading of blood borne, infectious diseases such as HIV virus (AIDS) and hepatitis B, among others.

In recognition of these problems the World Health Organization (WHO) has utilised and urged utilisation of auto-disable (AD) syringes, which have been made impossible to reuse for different structural reasons.

Such AD-syringes are often expensive to manufacture and therefore expensive to use, and many nations cannot afford to buy these kinds of disposable syringes to a necessary extent.

There exists a number of different AD-syringes which are used in connection with vaccination campaigns in the world's poorest countries. Besides containing individual auto disabling techniques, which most often require extra components compared to a normal or traditional syringe, some are also constructed to resist pressure filling, thereby preventing different kinds of attempts to reutilise the syringe.

From PCT/EP00/00028 an AD-syringe is known, which functions by disconnection of the piston from the plunger during emptying of the syringe, since the piston during the emptying sequence turns approximately 90 degrees and thus away from its interconnection with the plunger. The piston is then positioned at the bottom of the barrel and maintained there. The sealing surfaces of the piston have a significant vertical extension in the longitudinal axis of the barrel. The vertical extension of the piston's abutting surface causes the friction to be relatively low regardless whether the piston is in motion or not. The lubrication necessary for the utilisation of the syringe will thus, due to the large vertical abutting surface of the piston, be effective between piston and barrel inner wall regardless of motion or standstill. To resist pressure filling this approach is questionable since the necessary friction in order to resist pressure filling may not be achievable when the lubrication is permanently present in the abutting interface between piston and barrel inner wall.

Like the piston mentioned in the aforementioned patent application, pistons known from traditional syringes as well as AD-syringes are provided with one or more sealing surfaces to ensure tightness between piston and barrel inner wall which pistons are relatively permissive and which means that these, when mounted in the barrel with a diameter smaller than the piston's outside diameter, result in that the sealing surfaces' abutting surfaces are expanded significantly in the vertical direction and thus in the longitudinal axis of the barrel. The permanent presence of the lubrication in the area between the piston and the barrel inner wall means that with a given pressure through the needle one is able to impact and thereby position the piston to the starting position, whereby one will be able to reuse the syringe for a new injection.

Other AD-syringes are provided with a metal clip or one-way valve which efficiently shuts off pressure filling through the needle. Known AD-syringes thus alone avoid pressure filling as a result of the presence of an extra component.

This is because pistons in AD-syringes are predominantly unchanged compared to pistons in traditional syringes and therefore not themselves able to resist pressure refilling of the syringe which is a legal requirement for the AD-syringes that WHO wishes to utilise.

Manufacturing and assembly of the above described AD-syringes present a number of challenges. First, it is desirable to manufacture the syringes with as few components as possible to ensure a low manufacturing price and thereby a wide market in third world countries. Further, the syringes should comprise measures for preventing reutilisation both by regular filling or pressure filling of the syringe. For example, syringes with a releasable connection between piston and plunger, will not be prevented from reuse by pressure filling. Moreover, the previously mentioned solutions to prevent reuse are not suited for implementing in other types of AD-syringes, resulting in a wide variety of different solutions, none of them being co-operable. Finally, the AD-syringes should provide easy usability.

In view of the above the object of the present invention is providing an injector of the kind mentioned in the opening paragraph, that has a simple structure, is easy to operate for one time use, is inexpensive to manufacture, and cannot be reused.

SUMMARY OF THE INVENTION

With the first aspect of the invention this object is met by providing a piston for use in an injector comprising a cylinder having a longitudinal axis and an inner wall, which piston has a deformable sealing element with a convex surface, which deformable sealing element when the piston is inserted in the cylinder abuts the inner wall of the cylinder at an abutting interface and seals an annular gap between the piston and the inner wall of the cylinder, the abutting interface and the deformable sealing element having axial dimensions parallel with the longitudinal axis, characterised in that the ratio between the axial dimension of the abutting interface and the axial dimension of the deformable sealing element is in the range between 0.01 and 0.2. In another aspect the invention relates to an injector comprising the piston. In yet another aspect the invention relates to an injector comprising a cylinder with a longitudinal axis and an inner wall, and a piston having a deformable sealing element with a convex surface, which deformable sealing element abuts the inner wall of the cylinder at an abutting interface and seals an annular gap between the piston and the inner wall of the cylinder, the abutting interface and the deformable sealing element having axial dimensions parallel with the longitudinal axis, characterised in that the ratio between the axial dimension of the abutting interface and the axial dimension of the deformable sealing element is in the range between 0.01 and 0.2. In a further aspect the invention meets the object by providing the use in a disposable syringe of a piston having a deformable sealing element with a convex surface, which deformable sealing element upon mounting in the syringe abuts an inner wall of the syringe at an abutting interface and seals an annular gap between the piston and the inner wall of the syringe, the abutting interface and the deformable sealing element having axial dimensions parallel with a longitudinal axis of the syringe, wherein the ratio between the axial dimension of the abutting interface and the axial dimension of the deformable sealing element is in the range between 0.01 and 0.2. In specific embodiments the invention relates to the use in a disposable syringe of any embodiment of the piston of the invention.

At the location where the deformable sealing element abuts the inner wall of the cylinder the interface between the deformable sealing element and the inner wall will provide a static friction and a dynamic friction. Movement of the piston in the cylinder will require application of a force sufficient to overcome initially the static friction and subsequently the dynamic friction; the static friction will be larger than the dynamic friction and thereby the force to provide an initial movement of the piston is larger than the force required to provide a sustained movement of the piston. Once the piston has stopped moving the force to provide an initial movement must be overcome again. The present inventors have now surprisingly found that when the ratio between the axial dimension of the abutting interface and the axial dimension of the deformable sealing element is in the range between 0.01 and 0.4, e.g. between 0.01 and 0.2, between 0.01 and 0.15, between 0.01 and 0.1, between 0.01 and 0.05, etc., the piston, via the deformable sealing element, will provide a force on the inner wall of the cylinder, e.g. a static friction, that prevents movement of the piston in the cylinder within a range of forces typically available when attempting to refill a syringe using manual equipment, such as another syringe. In general, the inner wall of the cylinder requires lubrication in order to keep the dynamic friction sufficiently low to ensure sufficient glide for the piston and allow for easy movement of the piston in the cylinder and thereby easy delivery of a pharmaceutical composition during injection. Without being bound by theory the present inventors believe that for certain combinations of design of the deformable sealing element, i.e. when a piston according to the present invention is inserted in the cylinder, and choices of lubricant the deformable sealing element pushes the lubricant away from the surface of the inner wall of the cylinder to create a direct contact between the deformable sealing element and the inner wall thereby requiring a pressure of e.g. 300 kPa to create an initial movement, e.g. an axial initial movement, of the piston in cylinder. This is particularly relevant when the ratio between the axial dimension of the abutting interface and the axial dimension of the deformable sealing element is small, such as in the range between 0.01 to 0.1, e.g. between 0.01 and 0.05, and further it is even more relevant when the viscosity of the lubricant, e.g. a silicone oil lubricant, is also low, such as in the range between 500 cSt and 2,000 cSt, e.g. about 1,000 cSt. In general, the smaller the ratio between the axial dimension of the abutting interface and the axial dimension of the deformable sealing element the larger the force exerted via the deformable sealing element on the inner wall and thereby the larger the static friction between the inner wall and the deformable sealing element, e.g. at the abutting interface; the present inventors have found that the range between 0.01 and 0.4 is relevant for injectors of diameters traditionally used for delivery of pharmaceutical compositions, e.g. with inner diameters between about 2 mm and about 10 mm, although the inner diameter is not limited and will typically be up to 45 mm, such as in the range of 0.1 mm to 45 mm. The inner diameter may for example be about 10 mm, e.g. about 20 mm, about 30 mm, about 40 mm etc. In particular, since the axial dimension of the abutting interface is smaller than the axial dimension of the deformable sealing element the force exerted by the piston on the inner wall is focused, i.e. at the abutting interface, and will thereby maximise the friction created between the deformable sealing element and the inner wall. It is preferred that the ratio between the axial dimension of the abutting interface and the axial dimension of the deformable sealing element is in the range between 0.01 and 0.2, e.g. between 0.01 and 0.1, such as between 0.01 and 0.05. In general, the parameters may be selected in order to control the pressure required for an initial movement of the piston, and in other embodiments the required pressure is 250 kPa, 200 kPa, 150 kPa or 100 kPa.

The injector may be any kind of injector employed to deliver a pharmaceutical composition to a subject through the skin of the subject. For example, the injector may be a syringe, which is fitted with a hypodermic needle to inject a pharmaceutical composition, e.g. via subcutaneous (SC), intramuscular (IM), or intravenous (IV) delivery or another type of delivery, or the injector may be a needle free injector (NFI) capable of providing a narrow, high velocity fluid jet, which penetrates the skin and delivers the pharmaceutical composition to the subject, e.g. via SC or IM delivery. The injector may also take the form of a cartridge or a vial.

The injector comprises a cylinder. In the context of the invention a "cylinder" is any kind of tube or the like allowing the piston to be moved from one position in the cylinder to another. The cylinder will typically have an "actuating end" and "outlet end" opposite each other. The actuating end of the cylinder allows access to the piston for moving it, i.e. "actuating" the piston, in the cylinder. Likewise, the piston has an actuating surface facing the actuating end of the cylinder and an outlet surface opposite the actuating surface thus facing the outlet end of the cylinder.

In general, the distance from the actuating end of the cylinder to the outlet end of the cylinder minus the dimension of the piston parallel with the longitudinal axis of the cylinder defines an "operating length" of the cylinder. The piston may be moved towards the outlet end using any means from the actuating end, for example the piston may be moved towards the outlet end using a piston rod, a plunger or fluid pressure, e.g. gas or liquid pressure. It is particularly preferred that the piston cannot be moved towards the actuating end, e.g. from the outlet end, with engagement of the piston, e.g. with a piston rod or the like, from the actuating end. In a certain embodiment the injector does not comprise a piston rod. In another embodiment the injector comprises a piston rod.

The piston has a piston body and a deformable sealing element, which deformable sealing element abuts the inner wall of the cylinder at an abutting interface and seals an annular gap between the piston and the inner wall of the cylinder. The term "abutting interface" refers to any section where the inner wall and the deformable sealing elements contact each other and the "abutting interface" does not impose any limitations on either the inner wall of the cylinder or the surface of the sealing element. The piston will thus define an outlet section of the cylinder, i.e. at the outlet surface of the piston, of the piston, and an actuation section of the cylinder, i.e. at the actuating surface of the piston, and prevent fluid communication from the outlet section to the actuation section, or vice versa, past the piston. Movement of the piston in the cylinder towards the outlet end will thereby eject fluid present in the outlet section e.g. via an outlet. The piston body does not abut the inner wall of the cylinder, and only sealing elements present on the piston body abut the inner wall of the cylinder. The piston may have one or more deformable sealing elements as defined above although the piston may also have additional sealing elements with other shapes and functions. For example, the piston may have a supporting sealing element capable of guiding or controlling the orientation of the piston in the cylinder.

In a preferred embodiment the piston has two or more deformable sealing elements, and the piston is solid, i.e. it does not have a cavity or the like. A solid piston having two or more deformable sealing elements may be symmetrical relative to a transverse plane so that its orientation when inserted in the cylinder is not relevant. In contrast, an asymmetrical piston, e.g. a piston having a cavity, such as a cavity for housing a piston rod, needs to be oriented prior to insertion into the cylinder, e.g. so that the piston may be actuated by the piston rod inserted in the cavity. The removal of the need to orient the piston greatly simplifies production of syringes, e.g. prefilled syringes, and thereby reduces the production costs. It is preferred that the solid piston does not comprise any means to engage a piston rod. This embodiment is especially advantageous when used together with the piston rod of the present invention. For example, a solid piston without means for engaging a piston rod only allows that the piston is pushed by the piston rod, thereby emptying the cylinder.

The deformable sealing element and the abutting interface have axial dimensions, i.e. dimensions parallel with the longitudinal axis of the cylinder. The axial dimension of the deformable sealing element may also be referred to as the "height" of the deformable sealing element, and in general the axial dimension of the deformable sealing element is the largest axial dimension of the deformable sealing element. Likewise, the abutting interface also has an axial dimension that may be referred to as the "height" of the abutting interface. Correspondingly, the actuating end of the cylinder may be referred to as the upper end of the cylinder or injector and the outlet end may be referred to as the lower end.

In an embodiment of the invention initial movement of the piston requires a pressure of at least about 300 kPa. The initial movement may be in the axial direction of the cylinder of the injector. In particular, for a syringe with an inner diameter of around 4.65 mm a required pressure of 300 kPa is considered sufficient to prevent refilling of a syringe through the outlet using a manually operated syringe attached to the outlet. In other embodiments the pressure is at least 350 kPa, at least 400 kPa, at least 450 kPa, or at least 500 kPa. The minimum pressure of 300 kPa for creating an initial movement, e.g. an axial initial movement, is particularly advantageous for prefilled syringes, which need not be filled accurately by the end user as may be the case for syringes that are not prefilled.

In an embodiment of the invention the inner wall of the cylinder comprises a lubricant. By selecting parameters such as viscosity, e.g. kinematic viscosity, and amount of lubricant applied, the dynamic friction between the inner wall of the cylinder and the deformable sealing element is reduced or adjusted to a desired level. Medical grade silicone oil is the current industry standard for use as a syringe lubricant, but any suitable medical grade lubricant, such as glycerine, which will not interact adversely with the pharmaceutical composition, e.g. the drug medium, can be used. The lubricant may for example have a kinematic viscosity in the range of about 100 cSt to about 15,000 cSt, such as about 500 cSt to about 10,000 cSt, or about 1,000 cSt to about 8,000 cSt. The lubricant may be applied to the inner wall of the cylinder using any means as desired. For example, the lubricant may be sprayed on, e.g. by spraying it downwardly onto and into, the inner cylinder wall, resulting in the entire or parts of the inside surface of the cylinder being coated with lubricant. When the cylinder is made of a heat resistant material, e.g. glass, metal, or certain polymers, the lubricant may be applied using bake-on application technology. This technology generally involves the application of lubricant, e.g. silicone oil, as an emulsion, which is then baked on to the surface of the cylinder at a specific temperature and for a specific length of time. The lubricant may also be applied using a vapour phase deposition.

It is also possible that the entire or part of the piston surface, e.g. the surface of the deformable sealing element, may be coated with a lubricant. The lubricant on the piston surface may be of the same type as the lubricant used on the cylinder. Both the surface of the piston and the inner wall of the cylinder may comprise a lubricant or a lubricant may be applied to either the surface of the piston or the inner wall of the cylinder. In certain embodiments the pharmaceutical composition, e.g. a vaccine or a medicine, for injection via the injector serves as a lubricant. For example, the pharmaceutical composition may provide the only lubricant in the injector and no other lubricant needs to be used. In particular, the pharmaceutical composition may comprise an excipient, which provides, e.g. in addition to other functions, a lubricating effect in the injector. When the pharmaceutical composition provides a lubricating effect, the piston surface and/or the inner wall of the cylinder may not require any further lubricant, although it is also possible to employ an additional lubricant if desired.

The present inventors have observed that the effect of the deformable sealing element on the inner wall of the cylinder is more pronounced when the contact angles between the surface of the deformable sealing element and the inner wall of the cylinder are in the range of about 10° to about 30°, and yet more pronounced when the deformable sealing element is convex. Furthermore, when the deformable sealing element or the piston and the deformable sealing element has a Shore A hardness in the range of about 70 to about 90, e.g. about 70 to about 80, the effect is still more pronounced.

When the deformable sealing element pushes the lubricant away to create a direct contact between the deformable sealing element and the inner wall of the cylinder, the effect will be a high static friction to initiate movement of the piston, e.g. movement of the piston requires a pressure of at least 300 kPa, but once this static friction has been overcome the piston, i.e. the deformable sealing element, will be lubricated and the dynamic friction will be low to allow easy movement of the piston. When the movement of the piston is stopped the high static friction must be overcome again. This is especially advantageous for a disposable syringe that is intended not be refilled via the syringe or the outlet.

It is also possible to chemically functionalise the surface of the inner wall of the cylinder and/or the surface of the piston, e.g. the deformable sealing element and optional supporting sealing elements or the piston and the sealing elements, to provide smooth surfaces not requiring additional lubrication, e.g. from a lubricant. For example, the surfaces may be functionalised with perfluoro groups.

The piston comprises a deformable sealing element. In the context of the invention, the term "deformable" describes that the deformable sealing element may be deformed and thereby seal an annular gap between the piston and the inner wall of the cylinder. The deformable sealing element will thus have dimensions in a relaxed state, e.g. in a state without deformation, such as deformation caused by inserting the piston in a cylinder, and the diameter, e.g. of the piston including the deformable sealing element, in the relaxed state will be larger than the inner diameter of the cylinder of the injector. This ensures that the deformable sealing element will seal the annular gap between the piston and the inner wall of the cylinder. The diameter of the deformable sealing element is typically 3% to 20% larger than the inner diameter of the cylinder, e.g. 5% to 15% larger.

The deformable sealing element is made from a material of an appropriate hardness and elasticity to ensure that the annular gap between the piston and the inner wall of the cylinder is sealed. Any such material may be chosen for the deformable sealing element. In a preferred embodiment the piston of the invention is made by injection moulding from an appropriate thermoplastic polymer. Any thermoplastic elastomer may be used. Appropriate thermoplastic polymers comprise styrene block copolymers (SBCs), e.g. hydrogenated—H-SBC—(SEBS—styreneethylene butylenes-styrene or similar) or non hydrogenated (SBS—styrene-butadienestyrene) or alloys of these and other compatible polymers. Preferred SBCs are those known under the trademark Evoprene as marketed by AlphaGary Corporation (Leominster, Mass., USA). Evoprenes are described in the brochure "EVOPRENE™ Thermoplastic Elastomer (TPE) Compounds—GENERAL INFORMATION" (published by AlphaGary, July 2007), and preferred Evoprene™ polymers are Evoprene™ Super G, Evoprene™ G, Evoprene™ GC, and Evoprene™ HP, which are described in the brochures "EVOPRENE™ SUPER G Thermoplastic Elastomer (TPE) Compounds", "EVOPRENE™ G Thermoplastic Elastomer (TPE) Compounds", "EVOPRENE™ GC Thermoplastic Elastomer (TPE) Compounds", and EVOPRENE™ HP Thermoplastic Elastomer (TPE) Compounds (published by AlphaGary, July 2007), respectively. The contents of all mentioned brochures by AlphaGary are hereby incorporated by reference. When the piston is injection moulded the piston can be made with lower tolerances that afforded by technologies such as vulcanisation, which is commonly used in the manufacture of traditional rubber pistons. Appropriate materials comprise elastomers, such as rubbers, e.g. natural rubber, synthetic rubber (polyisoprene rubber, butyl rubber), silicone rubber, and the like, which may be defined with respect to e.g. the Shore durometer, which indicates the elasticity of the elastomeric material and measures the hardness of the elastomeric material, where the higher the durometer, the harder the compound. For example, in an embodiment of the invention the deformable sealing element or the piston and the deformable sealing element has a Shore A hardness in the range of about 50 to about 90, preferably 60 to 80, more preferred 71 to 76. The terms "Shore hardness" and "Shore durometer" may be used interchangeably. In general, the deformable sealing element will be homogeneous and composed of the same material throughout the volume of the deformable sealing element, which material has a Shore A hardness in the given ranges. By using a material with a Shore A hardness in the above mentioned range, a relatively hard elastomeric material is provided. This enables the piston to exert a sufficient force against the inner wall of the cylinder and thereby provide a static friction to resist a substantial pressure, e.g. 300 kPa, when it is exposed to e.g. pressure filling through the hypodermic needle. It should be noted that Shore A durometer is only one of many ways to characterise the material properties of the chosen material, and that other tests may also be employed to characterise the material.

The piston may be made from any material. In particular, the piston body is not in contact with the inner wall of the cylinder and the material of the piston body is generally only required to be inert with respect to any pharmaceutical composition in the injector. The deformable sealing element should likewise be inert with respect to the pharmaceutical composition in the injector. In a certain embodiment of the invention the piston and the deformable sealing element are of the same material, e.g. the piston body and the deformable sealing element are of the same material. By providing the piston, e.g. the piston body, and the deformable sealing element, and any optional supporting sealing elements, from the same material, a more cost-effective and simple production is made possible, thereby to a large extend avoiding different process steps e.g. time-consuming assembly.

In one embodiment of the invention the piston is dyed or pigmented, e.g. the piston is black, in order to provide contrast between the piston and the cylinder of the syringe. This contrast will allow more precise dosage when the cylinder comprises indications of the volume. For example, in a cylinder marked with black lines indicating volumes a black piston can make the indications more easily readable for better control of the volume aspired into or ejected from the injector. However, pigments and dyes may leach from the piston into the pharmaceutical composition in the injector. This is particularly relevant for injectors prefilled with a pharmaceutical composition since in this case the pharmaceutical composition may be in contact with the piston for long periods of time. In a preferred embodiment the piston of the invention does not comprise any pigments or dyes, e.g. the piston is "transparent". This is particularly preferred when the piston is used in an injector comprising a pharmaceutical composition, since there is no risk of leakage of dyes or pigments, nor is there an expressed need for contrast agents since the filling of the syringe is done by automated filling equipment.

The surface of the deformable sealing element may have any shape desired. In a certain embodiment the deformable sealing element has a convex surface, although the surface is not limited to convex shapes. In this context the term "convex" means that a straight line between any two points within the deformable sealing element does not cross the surface of the deformable sealing element. When the deformable sealing element has a convex surface the force exerted via the deformable sealing element on the inner wall of the cylinder will be maximised, since deformation of the deformable sealing element in a direction of the longitudinal axis of the cylinder is minimised. The convexity is particularly advantageous when the ratio between the axial dimension of the abutting interface and the axial dimension of the deformable sealing element is in the range between 0.01 and 0.2, e.g. between 0.01 and 0.1 or between 0.01 and 0.05, and in general the smaller the ratio between the axial dimension of the abutting interface and the axial dimension of the deformable sealing element the more pronounced the effect of the convex surface since the more focused the force exerted by the deformable sealing element on the inner wall of the cylinder.

The interface between the deformable sealing element and the inner wall of the cylinder will define contact angles, e.g. contact angles in a direction parallel with the longitudinal axis of the cylinder. In general, the contact angle between the surface of the deformable sealing element and the inner wall of the cylinder is in the range of from about 0° to about 50°. Specifically, on one side of a plane transverse to the cylinder, through the abutting interface, the convex surface of the deformable sealing element and the inner wall of the cylinder define a first contact angle in the range of from about 0° to about 50°, and on the other side of the plane the convex surface of the deformable sealing element and the inner wall of the cylinder define a second contact angle in the range of from about 0° to about 50°. A preferred range of contact angles is about 10° to about 30°. When these contact angles are below 50° the force exerted via the deformable sealing element on the inner wall of the cylinder are maximised so that the static friction will also be maximised. Furthermore, when the contact angles are below 50° the deformable sealing element is prevented from tilting. In the context of the invention the term "tilting" refers to a situation where the deformable sealing element upon application of a force in a direction of the longitudinal axis of the cylinder is deformed in the, generally, opposite direction. Tilting of the deformable sealing element may result in the static friction being reduced allowing easier movement of the piston towards either end of the cylinder. Tilting is generally also minimised when the piston comprises two or more deformable sealing elements. Thus, a tilting deformable sealing element may not be suitable for an AD-syringe. Tilting may furthermore create a risk that the volume of liquid ejected from the cylinder is difficult to control.

The cylinder may be made from any relevant material, and typical materials comprise polymeric materials, such as cyclic olefin copolymer (COC), e.g. TOPAS polymers (supplied by TOPAS Advanced Polymers GmbH), or polystyrene, or glasses. COC polymers are preferred due to their excellent barrier characteristics and thus accommodate the need for long-term storage of pharmaceutical agents. It is also contemplated that the cylinder may be made from a metal or it may comprise any combination of polymeric materials, glasses or metals. The cross-sectional shape of the cylinder is not limited although it is preferred that the cylinder has a round cross-section. It is also contemplated that the cross-section may be oval, elliptical, polygonal, etc. When the cylinder has a round cross-section the diameter, e.g. the inner diameter, may have any value conventionally used with syringes. For example, in a preferred embodiment the cylinder has an inner diameter in the range of about 2 mm to about 10 mm, such as 4.65 mm or 8.80 mm.

The cylinder at the actuating end of the cylinder may be open across the whole cross-section of the cylinder, which allows removal and insertion of the piston and thereby also filling of the injector via the actuating end. The cylinder may also have at the actuating end a ridge or protrusion(s) or the like preventing removal of the piston once inserted in the cylinder. In particular, the ridge or protrusion(s) may provide a "lock device" of a "spring-lock device" where the complementary "spring device" is contained on a piston rod. A spring-lock device or the like can lock the piston rod after moving the piston to the outlet end of the cylinder thereby preventing refilling of the cylinder.

When the injector is a syringe the cylinder may comprise, e.g. at the outlet end, a fitting for mounting a hypodermic needle. The cylinder may thus have an, e.g. tapered, end section with an outlet, e.g. a tubular outlet, from the cylinder providing or comprising an engagement device for engaging a complementary engagement device of a hypodermic needle, e.g. the engagement device and the complementary engagement device may comprise a male-female interaction, with the tubular outlet optionally comprising an external thread, e.g. a helical external thread, and the hypodermic needle optionally comprising a complementary internal thread, e.g. a helical internal thread. A hypodermic needle may be fitted to allow simple removal, and replacement, of the hypodermic needle, or the hypodermic needle may be mounted permanently on the injector. In particular, the hypodermic needle may be mounted on the injector so that its removal requires the destruction of the injector thereby preventing reuse, e.g. by mounting a new hypodermic needle, and also limiting refilling the injector from the outlet end to be via the hypodermic needle, which is cumbersome and inefficient. When the injector is a NFI the outlet tube may be sufficiently narrow to provide an outlet stream of a velocity sufficient to penetrate the skin of a subject. The outlet tube of a NFI may be designed for engaging with a closing member; the same engagement devices are relevant for the closing member and the NFI as are used with an injector with a hypodermic needle.

In an embodiment of the invention the injector, preferably prefilled, is a syringe with a hypodermic needle. The syringe may have a hypodermic needle mounted, e.g. permanently mounted, on a tubular outlet or an outlet of another shape, and the injector may further comprise a hypodermic needle protection cap that protects the user from premature contact with the hypodermic needle. When the injector is prefilled, in particular when it also comprises a piston rod, there may be a clearance between the actuating end of the cylinder and the actuating surface of the piston. The clearance ensures stability of a piston rod when this is inserted in the cylinder, which results in a safer and easier operation of the injector. The clearance, e.g. measured in units of length, may be any value relevant for the size, e.g. volume, of injector and the dose of pharmaceutical composition in the injector. Typical values for the clearance are between about 2 mm to about 20 mm.

In a preferred embodiment the injector comprises a piston rod, which also serves as a needle protection cap. A piston rod may also be referred to as a plunger, and in the context of the invention the two terms may be used interchangeably.

In this embodiment the injector is a syringe with a hypodermic needle mounted, e.g. permanently mounted, on a tubular outlet or an outlet of another shape. For example, the piston rod may have a tubular section for housing the hypodermic needle the tubular section having a needle insertion end comprising an engagement device for engaging a complementary engagement device of the outlet or the hypodermic needle, and a needle protection end opposite the needle insertion end, which tubular section comprises a device for actuating the piston, characterised in that a length of the tubular section is equal to or larger than the operating length of the cylinder. In one embodiment the piston rod has a tubular section for housing the hypodermic needle and an operating section, which tubular section comprises an engagement device for engaging a complementary engagement device of the outlet or the hypodermic needle, and which operating section comprises a device for actuating the piston, wherein the combined length of the tubular section and the operating section is larger than the operating length of the cylinder.

The piston rod has a needle insertion end, i.e. the end of the piston rod facing the outlet end of the cylinder when it is mounted on a syringe, and a needle protection end opposite the needle insertion end. The device for actuating the piston may be at either end of the piston rod. The piston rod will typically be from about 1 mm to about 20 mm longer than the operating length. In certain embodiments the length of the piston rod is equal to the operating length of the cylinder. The tubular section, e.g. the tubular section and the operating section, may take any form appropriate for their respective functions. For example, in its simplest form the piston rod is a tube of a material sufficiently rigid to push the piston from the actuating end to the outlet end of the cylinder, which tube has a smaller outer diameter than the inner diameter of the cylinder and an inner diameter providing an engagement device for engaging the outlet of the cylinder or the hypodermic needle, thus providing the complementary engagement device.

In one embodiment, which is particularly relevant for large syringes, e.g. of a volume of 2 to 5 ml or more, the inside walls of the tubular section comprise axial ridges, e.g. 3, 4 or more, at the needle insertion end, which ridges provide an engagement device for engaging the outlet of the syringe or the hypodermic needle. This will allow that the tubular section can be of a sufficiently large diameter to ensure stable actuation of the piston in the syringe. It is generally preferred that ratio of the outer diameter of the tubular section to the inside diameter of the cylinder is in the range of 50% to 90%, such as in the range of 80% to 90%. When the ratio is 50% or higher, e.g. about 80% or higher, the piston can be actuated with sufficient stability to ensure correct operation of the syringe. It is particularly preferred that the injector is prefilled when it comprises a piston rod.

The device for actuating the piston may be any device that can actuate the piston, in particular push the piston towards the outlet end of the cylinder. The device for actuating the piston may be located at either end of the piston rod. For example, the device for actuating the piston may be at the needle insertion end, or the device for actuating the piston may be at the needle protection end. The device for actuating the piston may also be referred to as the "actuating device" and the terms may be used interchangeably throughout this document. The device for actuating the piston may be a flat surface of a rigid material. In one embodiment the device for actuating the piston comprises a surface of a shape complementary to the actuating surface of the piston. For example, the piston may comprise a concave, or hollow, region with the concave surface constituting the actuating surface, and the device for actuating the piston may comprise a complementary convex surface. In a preferred embodiment the actuating device is at the needle insertion end and is used in combination with a solid piston. For example, the surface of the actuating device is less than the piston's surface area, e.g. the total surface area perpendicular to the longitudinal axis of the cylinder. When the device for actuating the piston and the piston have surfaces of complementary shapes the complementarity provides stability when the piston rod is used to actuate the piston. This in turn ensures correct use of the syringe and more precise ejection of a pharmaceutical composition from the syringe. Likewise, the actuating surface may be convex and the device for actuating the piston may be a complementary concave surface. In general, it is preferred that the piston is solid and does not comprise a cavity. In general, the device for actuating the piston does not comprise means for engaging the piston. In particular, the device for actuating the piston cannot move the piston towards the actuating end of the cylinder and thereby the injector cannot be refilled using the piston rod of the invention. It is preferred that the device for actuating the piston has a concave surface or shape which is complementary to a convex actuating surface of the piston. For example, the piston may have a conical actuating surface, e.g. a convex conical actuating surface, and the device for actuating the piston may have a concave surface or structure of complementary shape. It is preferred that the piston has a convex conical actuating surface for interaction with the device for actuating the piston. It is further preferred that the piston is symmetrical and has convex conical surfaces at both ends so that it can be inserted in the cylinder of the syringe without regard to orientation. A convex conical surface is further advantageous since it ensures that the cylinder of the syringe is emptied more efficiently.

In a specific embodiment the piston rod comprises, e.g. on the outside surface of the tubular section, one or more guidance structures for axially guiding the piston rod when it is inserted in the cylinder of the injector. With the axial guidance provided by the guidance structures insertion of the piston rod into the cylinder and also movement of the piston rod towards the outlet end of the syringe is made easier and more stable. The guidance structures, e.g. 2, 3 or 4 guidance structures, generally comprise protrusions that can contact the inner surface of the cylinder and thereby ensure that movement of the piston rod in the cylinder will be parallel to the axial dimension of the cylinder. For example, the guidance structures may comprise 2 to 4 protrusions in the form of rails evenly distributed on the circumference of the cylinder; the rails will typically have a length of at least 10% of the operating length, although shorter and longer rails are also contemplated. In another embodiment the piston rod comprises a single guidance structure, which is a helical ridge on the outside of the tubular section.

The length of the tubular section, e.g. the combined length of the tubular section and the operating section, may be the combined length in any direction. It is preferred that the tubular section over the length of the tubular section has cross-sectional dimensions allowing the device for actuating the piston to actuate the piston throughout the operating length of the cylinder, for example the cross-sectional dimensions are smaller than the inner diameter of the cylinder.

The tubular section houses the hypodermic needle when the piston rod is mounted on the hypodermic needle as a protection cap. The tubular section comprises an engagement device for engaging a complementary engagement device of the outlet or the hypodermic needle. The engagement device and its complementary engagement device may involve any type of engagement, such as a male-female interaction, with the tubular outlet or hypodermic needle optionally comprising an external thread, e.g. a helical external thread, and the tubular section correspondingly comprising a complementary internal thread, e.g. a helical internal thread. The engagement device and its complementary engagement device may also involve magnetic forces or a press-fit interaction.

In one embodiment the tubular section of the piston rod contains an elastomeric material for sealing the hypodermic needle. The elastomeric material is located so that the tip of a hypodermic needle is sealed by the elastomeric material when the hypodermic needle is inserted into the tubular section and thereby into the elastomeric material. For example, the elastomeric material may be located at the needle protection end of the piston rod. When a piston rod is required to be significantly longer than the hypodermic needle the elastomeric material may be located at any position in the tubular section where the tip of the hypodermic needle will be inserted into the elastomeric material, when the hypodermic needle is inserted into the tubular section. The elastomeric material will seal the tip of the hypodermic needle and prevent the content of the syringe from leaking or evaporating. The elastomeric material will also prevent contaminants from entering into the cylinder and thus prevent the contamination of a pharmaceutical composition, e.g. a drug or a vaccine, in the cylinder. A piston rod with the elastomeric material is therefore especially relevant for a prefilled syringe. The elastomeric material may be any elastomeric material capable of sealing the hypodermic needle. It is preferred that the elastomeric material does not leak components, e.g. dyes, plasticisers, monomers or the like, to the contents of the syringe. An exemplary elastomeric material is a chemically inert thermoplastic elastomer, e.g. of a medical grade, such as a silicone rubber or an SBC as defined above.

In a certain embodiment the piston rod incorporates an opening at its needle protection end so that the elastomeric material can be inserted from the needle insertion end via the opening. This enables insertion of the elastomeric material from the outside and towards the inward hollow of the piston rod, which may also contain inward protrusions, e.g. 2 to 6 inward protrusions. Inward protrusions can guide the elastomeric material and also fix the elastomeric material in the piston rod. In a specific embodiment the inward protrusions, e.g. the piston rod has 4 inward protrusions, are ridges, which are parallel with the longitudinal axis of the piston rod. It is further preferred that the elastomeric material has detents or recesses complementary to these ridges to further improve guidance and fixing of the elastomeric material.

In a specific embodiment the piston rod comprises, at either end, a thumb-plate which, when the piston rod is inserted in the cylinder, may be used for pushing, e.g. with a finger, the piston towards the outlet end of the cylinder using the piston rod. The thumb-plate may have any size, e.g. with respect to the cross-sectional area, as deemed appropriate for the intended use. However, the thumb-plate typically has a larger cross-sectional area than the cross-sectional area of the cylinder. For example, the thumb-plate may be round and have a diameter of up to twice the inner diameter of the cylinder. The presence of a thumb-plate increases the stability during administration of the injection which is of great importance when exercising human injections. Furthermore, the thumb plate increases user comfort when operating the syringe, which is especially relevant during injections with larger syringes where the force needed to initiate movement of the piston (break loose force) is substantial compared to smaller syringes. Consequently, the thumb plate area is typically increased with increased cylinder diameter of which the latter is the governing parameter for the force needed to empty the cylinder. The thumb-plate may have any shape but it will typically be a disc or an annular ring. An annular ring placed at the needle insertion end may allow insertion of a hypodermic needle into the section for housing the hypodermic needle. When placed at the needle protection end an annular ring, e.g. an annular ring having opening for insertion of the elastomeric material, may allow introduction of the elastomeric material into the tubular section via either end of the piston rod. In a preferred embodiment the thumb-plate is present at the needle protection end of the piston rod, and the piston rod has a generally cylindrical shape. In this embodiment it is further preferred that the thumb-plate is disc shaped. In a particularly preferred embodiment the piston rod is cylindrical, has a disc shaped thumb-plate at the needle protection end and contains an elastomeric material for sealing the hypodermic needle. In a certain embodiment the piston rod, optionally having a thumb plate located at the needle protection end, has a length, e.g. a total length, which is equal to the operating length of the cylinder. In this embodiment the piston rod, e.g. including the optional thumb plate, has a cross-sectional area, which is equal to or less than the inner cross-sectional area of the cylinder, e.g. the piston rod has a diameter, which is equal to or less than the inner diameter of the cylinder. Thus, the piston rod will be fully inserted into the cylinder after finalisation of the injection so that the piston rod cannot readily be removed from the cylinder.

In a specific embodiment the piston rod is a single generally frustoconical piece with the wide end of the frustocone comprising the engagement device and the narrow end comprising the actuating device. The hypodermic needle is thus inserted into the tubular section from the wide end of the frustocone. The wide end may further comprise a finger grip for easier handling of the piston rod in the injector. The finger grip may take the form of a narrow section of the frustocone with a smaller diameter than found for the generally frustoconical shape; this narrow section thus allows a better grip on the piston rod when the piston rod is removed from the hypodermic needle, and the narrow section further allows a better grip when the piston rod is inserted in the cylinder for actuating the piston. The narrow end of the frustocone may represent an operating section, and this part of the frustocone may be hollow or solid. The actuating device may take any form described above and the operating section may be part of the frustocone or it may be cylindrical in shape.

In a further preferred embodiment the piston rod, e.g. with a frustoconical or tubular shape, and the cylinder comprise complementary parts of a spring-lock device, e.g. barbs or the like, that locks the piston rod in place in the cylinder once the piston has been inserted in the cylinder and moved to a certain distance towards the outlet end, e.g. moved to the full operating length, with the aid of the complementary part of the spring-lock device. For example, the piston rod may comprise the "spring device" of the spring-lock device and the cylinder, e.g. the inner wall of the cylinder, may comprise the "lock device" of the spring-lock device, or vice versa. In an specific embodiment the cylinder comprises at the actuating end, as a "lock device" a ridge or protrusion(s) or the like facing the inner wall of the cylinder and the piston rod, e.g. at a frustoconical section with the narrow end facing the actuating device and a broader end with a larger diameter than the distance between the protrusions or a larger diameter than the ridge, may comprise a resilient material, as the "spring device", allowing insertion of the piston rod in the cylinder. Once the resilient material has been inserted past the protrusion(s) or ridge, the piston rod is locked in placed and cannot be removed from the cylinder. Thereby refilling and reuse of the injector is prevented.

The injector is suitable for delivery of a pharmaceutical composition to a subject. Any type of pharmaceutical composition for transdermal delivery may be employed in the injector. For example, the pharmaceutical composition may be a vaccine or a medicine. In an embodiment of the invention the cylinder, e.g. the outlet section of the cylinder, is prefilled with a pharmaceutical composition. It is preferred that the cylinder is prefilled with the pharmaceutical composition in the correct dose for delivery to the subject although it is also contemplated that the cylinder may be prefilled with a larger dose than intended for the subject in order to provide a more flexible product. An injector of the invention, which is prefilled with a pharmaceutical composition, may comprise a hypodermic needle, e.g. a hypodermic needle with a protection cap, or the prefilled injector does not comprise a hypodermic needle. Regardless of the presence of a hypodermic needle the injector advantageously can be supplied without a traditional piston rod attached to the piston. When the injector does not comprise a traditional piston rod attached to the piston packaging and storage of the prefilled injector is simplified due to a lower requirement for space. In particular, for injectors prefilled with a pharmaceutical composition requiring cooling, e.g. a vaccine, injectors without a traditional piston rod may be packed more closely thereby reducing the power consumption for cooling. This is especially relevant for supplying the prefilled injectors for developing countries or similar regions. A prefilled injector having a traditional piston rod attached to or engaged with a piston in the injector introduces the risk that the injector is emptied prematurely. This risk does not exist for an injector without a piston rod attached to or engaged with a piston.

In another aspect the invention relates to a piston rod for an injector, especially for an injector as described above. The piston rod may be for an injector according to any embodiment described above where the injector comprises a hypodermic needle. The piston rod may also be for an injector not according to the present invention, for example an injector having an alternative piston to the piston described above. In general, the alternative piston will have a deformable sealing element with a surface, e.g. a convex surface, which deformable sealing element when the piston is inserted in the cylinder abuts the inner wall of the cylinder at an abutting interface and seals an annular gap between the piston and the inner wall of the cylinder. All other features of this alternative piston may be as the piston of the present invention. The same advantages observed for the piston of the present invention will be observed when the alternative piston is employed, except that initial movement of the alternative piston does not require a pressure of at least about 300 kPa. For example, initial movement of the piston in this aspect may require a pressure in the range of from 10 kPa to 100 kPa.

In general, the injector, e.g. having the piston of the invention or the alternative piston, comprises a hypodermic needle attached to an outlet at an outlet end of the cylinder opposite an actuating end of the cylinder. The cylinder has an operating length defined by the distance from the actuating end of the cylinder to the outlet end of the cylinder minus the dimension of the piston parallel with the longitudinal axis. The piston rod of the invention has a tubular section for housing the hypodermic needle the tubular section having a needle insertion end comprising an engagement device for engaging a complementary engagement device of the outlet or the hypodermic needle, and a needle protection end opposite the needle insertion end, which tubular section comprises a device for actuating the piston, characterised in that a length of the tubular section is equal to or larger than the operating length of the cylinder. The piston rod may comprise any of the features or combination of features for the piston rod described above. The piston rod is especially advantageous when used with a prefilled injector since this removes the need for a separate piston rod and thereby fewer parts are needed for the prefilled injector, which is relevant when the injector is intended for markets, e.g. vaccination campaigns in developing countries, where it is crucial to minimise the manufacturing costs.

It is noted that the piston rod of the invention is not limited to injectors of the invention and in a further aspect the invention relates to a piston rod for an injector, which comprises a cylinder with an inner wall, a piston having a deformable sealing element, which deformable sealing element abuts the inner wall of the cylinder at an abutting interface and seals an annular gap between the piston and the inner wall of the cylinder, and a hypodermic needle attached to an outlet at an outlet end of the cylinder opposite an actuating end of the cylinder, the cylinder having an operating length defined by the distance from the actuating end of the cylinder to the outlet end of the cylinder minus the dimension of the piston parallel with the longitudinal axis, the piston rod having a tubular section for housing the hypodermic needle the tubular section having a needle insertion end comprising an engagement device for engaging a complementary engagement device of the outlet or the hypodermic needle, and a needle protection end opposite the needle insertion end, which tubular section comprises a device for actuating the piston, characterised in that a length of the tubular section is equal to or larger than the operating length of the cylinder.

In yet another aspect, the invention relates to an injector comprising a cylinder with an inner wall, a piston having a deformable sealing element, which deformable sealing element abuts the inner wall of the cylinder at an abutting interface and seals an annular gap between the piston and the inner wall of the cylinder, and a hypodermic needle attached to an outlet at an outlet end of the cylinder opposite an actuating end of the cylinder, the cylinder having an operating length defined by the distance from the actuating end of the cylinder to the outlet end of the cylinder minus the dimension of the piston parallel with the longitudinal axis, and a piston rod having a tubular section for housing the hypodermic needle the tubular section having a needle insertion end comprising an engagement device for engaging a complementary engagement device of the outlet or the hypodermic needle, and a needle protection end opposite the needle insertion end, which tubular section comprises a device for actuating the piston, characterised in that a length of the tubular section is equal to or larger than the operating length of the cylinder.

In yet another aspect the invention relates to an injector comprising a cylinder with a longitudinal axis and an inner wall, a piston having a deformable sealing element, which deformable sealing element abuts the inner wall of the cylinder at an abutting interface and seals an annular gap between the piston and the inner wall of the cylinder, and a piston rod having a tubular section for housing the hypodermic needle, the tubular section having a needle insertion end comprising an engagement device for engaging a complementary engagement device of the outlet or the hypodermic needle, and a needle protection end opposite the needle insertion end, which tubular section comprises a device for actuating the piston, wherein a length of the tubular section is larger than the operating length of the cylinder, and wherein the tubular section contains an elastomeric material for sealing the hypodermic needle. It is preferred that the piston has two or more deformable sealing elements, and the piston is solid; this piston advantageously does not require a specific orientation in the cylinder. It is further preferred that the piston has a convex actuating surface and that the device for actuating the piston has a concave surface or structure of complementary shape. It is also preferred in this aspect that initial movement of the piston requires a pressure of less than about 300 kPa, e.g. initial movement requires a pressure in the range of 10 kPa to 100 kPa. The injector may have a hypodermic needle, e.g. attached at the outlet of the injector, or the injector does not have a hypodermic needle. In another embodiment of this aspect the injector is prefilled with a pharmaceutical composition. In the context of the invention a "pharmaceutical composition" is considered to be any composition intended for injection into a subject, and it may comprise vaccines, medicines, medicaments, drugs, cosmetic compositions, saline etc.

In another aspect the invention relates to a kit of parts comprising the piston rod of the invention and a hypodermic needle, e.g. with the hypodermic needle inserted in the tubular section for housing the hypodermic needle of the piston rod. This aspect may also have an injector but the injector is not required. For example, the hypodermic needle may be of a standard size for mounting on a syringe of a standard size with a corresponding predefined operating length; the piston rod will be longer than the operating length of the cylinder. The kit of parts may thus be supplied to fit a standard syringe, e.g. with indications of the size of the syringe for which the piston rod, and e.g. the hypodermic needle, is suited. The kit of parts may also contain a piston appropriate for the size of the syringe. In general, all features described above for the first aspect of the invention relating to the piston are relevant for all other aspects of the invention and though not explicitly stated, the features may be combined freely taking into account the necessary limitations described for an individual feature or a set of features. Likewise all features and corresponding advantages observed for any embodiment of the aspects relating to injectors of the invention may be combined freely, only constrained as indicated specifically for individual features.

The invention is described further below with reference to the Figures.

BRIEF SUMMARY OF THE DRAWINGS

FIG. 5 shows a longitudinal cross section of an embodiment of the injector of the invention.

The different embodiments are modifications and variations of a piston and the same reference numerals have been used for like parts.

DETAILED DESCRIPTION OF EMBODIMENT OF THE INVENTION

The present invention will now be described in greater detail with reference to the appended drawings.

Figure 1:
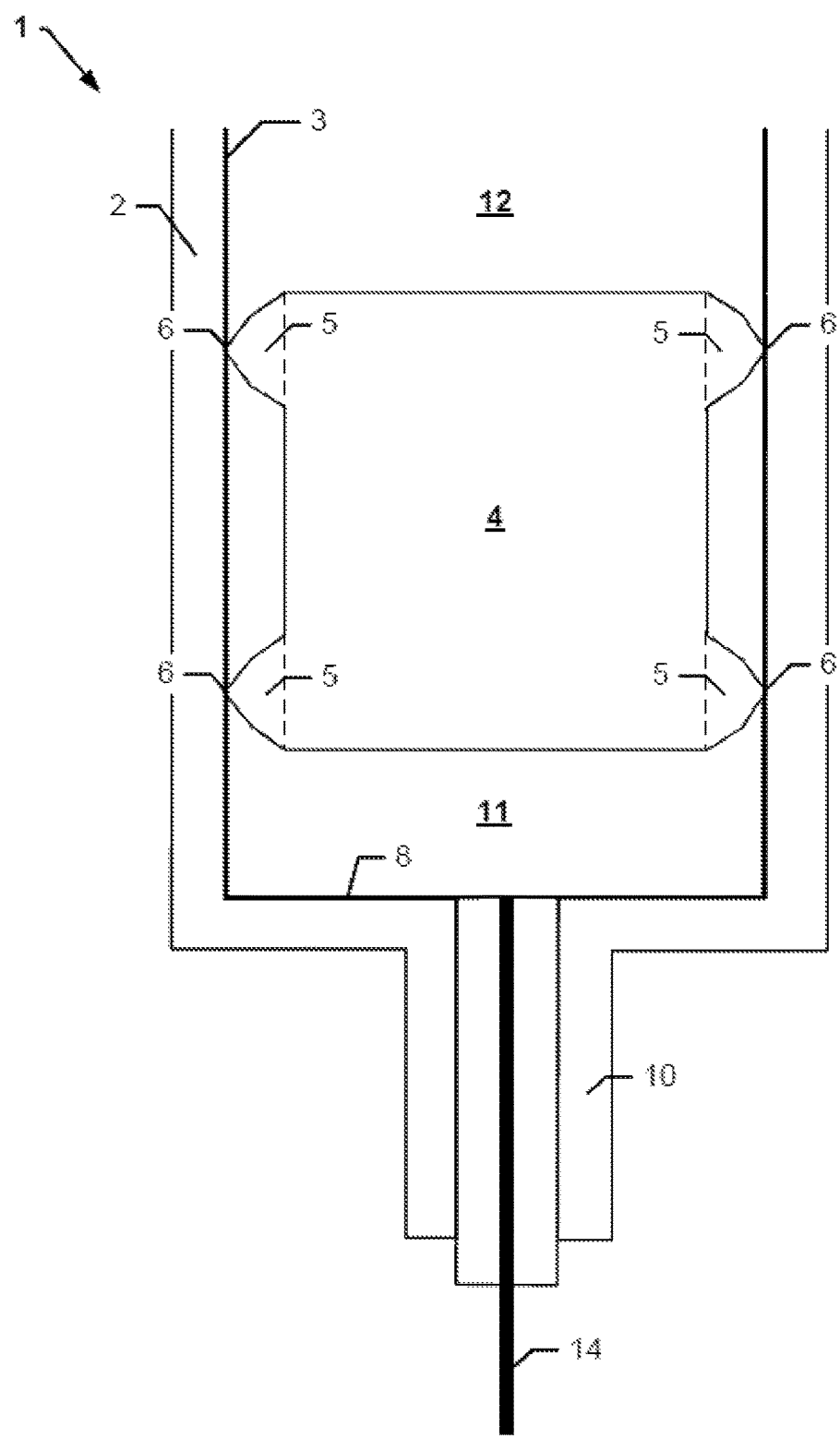
FIG. 1 shows a longitudinal cross section of an embodiment of the injector of the invention.

FIG. 1 shows a cross-section of an injector 1. The injector comprises a cylinder 2 with an inner wall 3 and a piston 4, having two deformable sealing elements 5 with convex surfaces. The deformable sealing element 5 abuts the inner wall 3 of the cylinder 2 at an abutting interface 6 and seals an annular gap between the piston 4 and the inner wall 3 of the cylinder 2. The abutting interface 6 and the deformable sealing element 5 have axial dimensions parallel with a longitudinal axis of the cylinder 2, and the ratio between the axial dimension of the abutting interface 6 and the axial dimension of the deformable sealing element 5 is in the range between 0.01 and 0.4, such as between 0.01 and 0.2. The piston 4 shown in FIG. 1 is solid and does not have a cavity. The piston 4 shown in FIG. 1 is symmetrical relative to a transverse plane. The piston 4 in FIG. 1 is illustrated with two deformable sealing elements although the piston 4 may also have one or more than two deformable sealing elements.

In the embodiment shown the piston 4 comprises two circumferential deformable sealing elements 5, positioned at a distance from each other in a longitudinal direction of the piston 4, each being adjacent to an end of the piston 4. Each deformable sealing element 5 comprises a convex surface extending at an angle from the piston 4 towards the inner wall 3 of the cylinder 2.

The abutting interface 6 has a height extending along the longitudinal axis of the cylinder 2. The abutting interfaces 6 of each deformable sealing element 5 may have different heights, and the abutting interface 6 of each deformable sealing element 5 need not be uniform along the circumference of the inner wall 3, as long as the ratio between the axial dimension of the abutting interface 6 and the axial dimension of the deformable sealing element 5 is in the indicated range.

In the embodiment shown, the convex surfaces meet the inner wall at an angle, thereby providing an approximately punctuated abutting interface 6. The abutting interface 6 provides for a force exerted on the inner wall 3 by the piston 4 via the deformable sealing element 5, as a result of the diameter of the piston 4 including the deformable sealing element 5, being larger than the inner diameter of the cylinder 2.

The deformable sealing elements 5 divide the cylinder in different sections in the longitudinal direction. The uppermost deformable sealing element 5 defines an actuation section 12 of the cylinder, in which a piston rod (not shown) may be inserted to move the piston 4. The lowermost deformable sealing element 5 defines an outlet section 11, in which a liquid 7 for injection, e.g. a pharmaceutical composition, may be located. The actuation section 12 and outlet section 11 may vary with the position of the piston 4. The deformable sealing elements 5 ensure that liquid 7 in the outlet section 11 does not pass through or past the piston 4 to the actuation section 12. Although two deformable sealing elements 5 are illustrated, any number of deformable sealing elements 5 may be utilised. For example, in other embodiments the piston 4 comprises 3, 4, 5 or more deformable sealing elements 5. In general the more deformable sealing elements 5 the larger the force required for initial movement of the piston 4.

The cylinder comprises an actuating end 9 and an outlet end 8 positioned at each end of the cylinder 2. The actuating end 9 defines the end in which the piston 4 may initially be inserted. The outlet end 8 defines the end towards which the piston 4 is moved during operation, e.g. emptying the injector 1.

A hypodermic needle 14 is here shown premounted at a tubular outlet 10. The tubular outlet 10 being connected to the outlet end 8 of the cylinder 2. The tubular outlet 10 may be an integral part of the cylinder 2. The tubular outlet 10 may have any form that allows engagement with a hypodermic needle using an appropriate principle, such as in a male-female relationship, as to attach the hypodermic needle 14 to the cylinder 2.

The injector 1 may further comprise a piston rod (not shown). By inserting the piston rod through the actuating end 9 of the cylinder 2, the piston rod enables the piston 4 to be moved towards the outlet end 8. By pushing the piston rod into the cylinder 2, the piston 4 is moved towards the outlet end 8, forcing liquid 7 from the outlet section 11 out through the hypodermic needle 14 or outlet 10.

During injection of liquid 7 from the injector 1, an ejecting force is applied by, for example a piston rod (not shown), to the actuating surface of the piston 4 and in the direction of the outlet end 8 of the cylinder. Since the outlet section 11 is filled with a liquid 7, the liquid 7 creates an opposing force in a direction opposite the ejecting force. The piston 4 therefore undergoes a compression as a result of the ejecting force and the opposing force. As a result, the force on the inner wall is enlarged which causes the piston 4 and deformable sealing elements 5 to expand radially and seal more tightly against the inner wall 3, thereby preventing liquid 7 from passing from the outlet section 11 to the actuation section 12, and likewise ensuring that the correct dose of liquid 7 is discharged and injected from the injector 1. It should be understood that movement of the piston 4 in the aforementioned direction, occurs when the ejecting force exceeds the force and the static friction created at the abutting interface 6 by the force on the inner wall 3. Likewise, if it is attempted to refill the cylinder 2 via pressure filling through the hypodermic needle 14, the opposing force has to exceed the static friction created at the abutting interface 6 by the force on the inner wall 3. Initial movement of the piston 4 requires a pressure of at least about 300 kPa.

The inner wall 3 of the cylinder 2 comprises a lubricant, such as a silicone oil or a vaccine or another pharmaceutical composition, for easier movement, e.g. to lower the dynamic friction, of the piston 4 in the cylinder 2.

Figure 2:
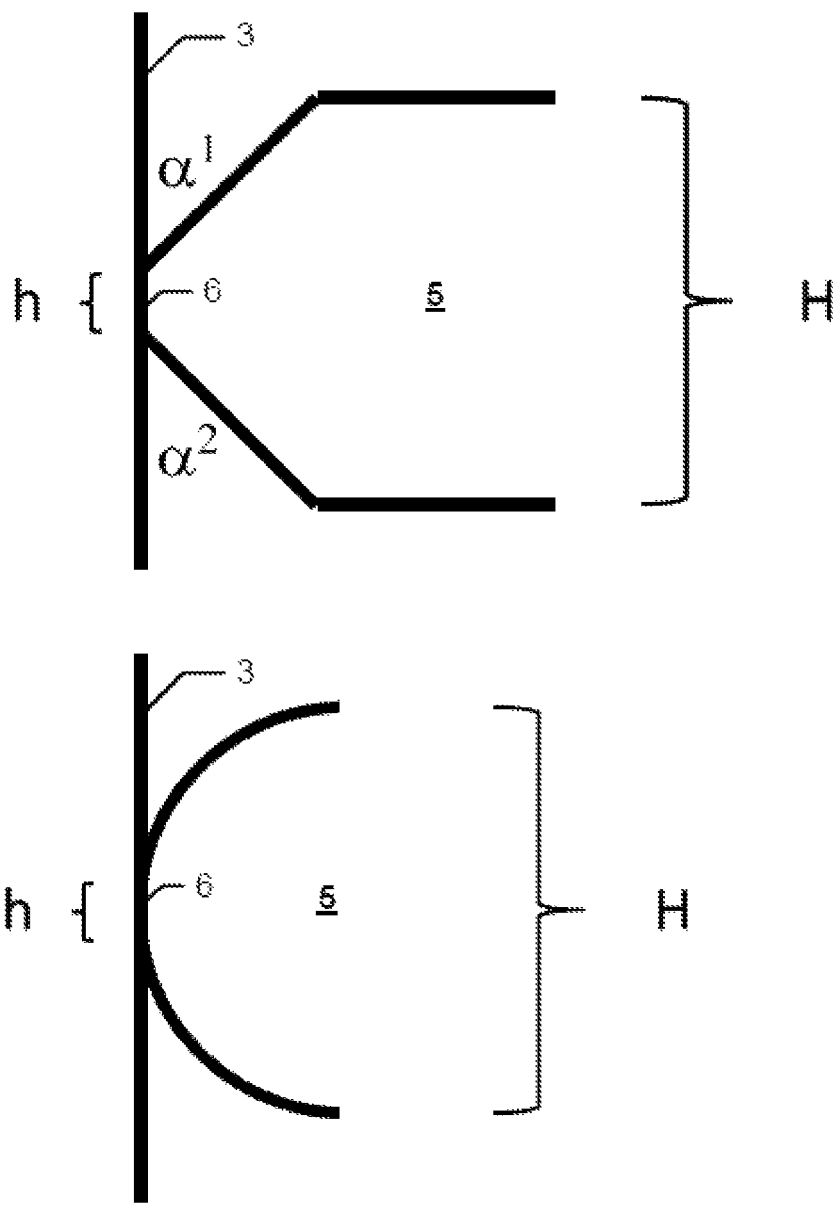
FIG. 2 shows two embodiments of the deformable sealing element of the injector of the invention.

FIG. 2 shows different embodiments of the invention with differently shaped deformable sealing elements 5. In the embodiment of FIG. 2 cross-sections of the deformable sealing elements 5 and inner wall 3 of a cylinder 2 are shown. The height of the deformable sealing elements 5 is denoted H. On each side of a plane (not shown) transverse to the cylinder 2, through the abutting interface 6, the convex surface of the deformable sealing element 5 and the inner wall 3 of the cylinder 2 define contact angles $\alpha^1$, $\alpha^2$, respectively. The angles $\alpha^1$, $\alpha^2$ are approximately 45°. The angles $\alpha^1$, $\alpha^2$ may be in the range from about 0° to about 50°, and can vary independently of each other. The convex surface of the deformable sealing element 5 may be of any shape, not limited to linear lines forming the convex surface.

The abutting interface 6 is defined by the surface at which the deformable sealing element 5 abuts the inner wall 3. The abutting interface 6 has a height denoted h. The ratio between the axial dimension of the abutting interface 6 and the axial dimension of the deformable sealing element 5 is about 0.1 to about 0.15. The ratio between the axial dimension of the abutting interface 6 and the axial dimension of the deformable sealing element 5 may, however, be in the range between 0.01 and 0.4, e.g. between 0.01 and 0.2.

Figure 3:
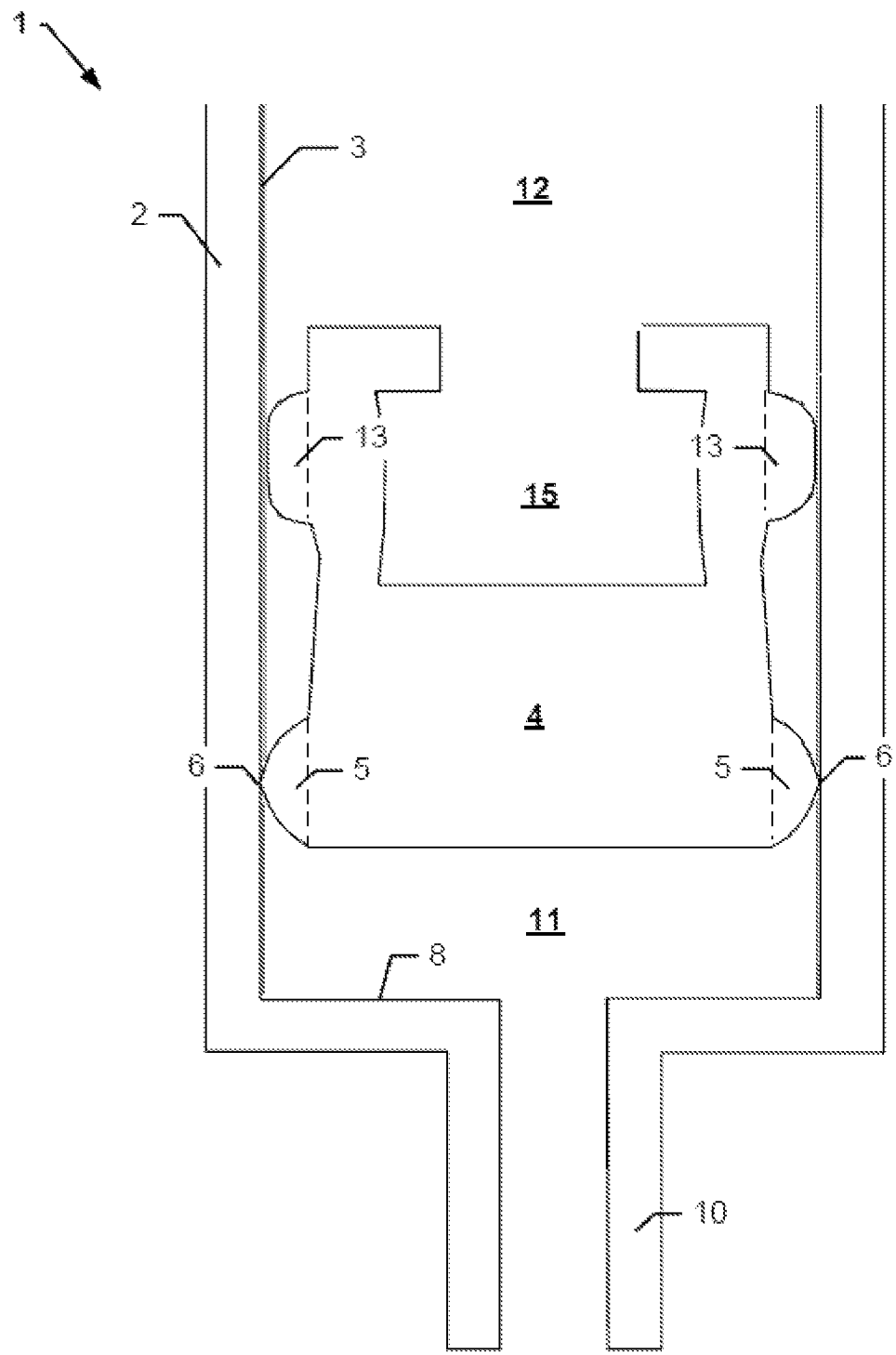
FIG. 3 shows a longitudinal cross section of an embodiment of the injector of the invention.

FIG. 3 shows an embodiment of the injector of the invention where the piston 4 comprises a cavity 15, positioned adjacent to a supporting sealing element 13, and surrounded totally or partly on all sides by the piston 4. During use, the cavity 15 can house a tip of a piston rod (not shown), through a hole in the actuating surface of the piston 4. The cavity 15 may be of any shape desired.

The deformable sealing element 5 and the supporting sealing element 13 may be of any shape independently of each other. In the shown embodiment, the lowermost, deformable sealing element 5 has the same characteristics as the deformable sealing elements 5 described in FIG. 1. The uppermost, supporting sealing element 13 has a different profile resulting in a lager contact interface with the inner wall 3 than required to provide a ratio between the axial dimension of the contact interface and the axial dimension of the supporting sealing element below 0.4. The uppermost, supporting sealing element 13 does not provide a significantly increased static friction but guides the piston 4 during movement, to control the orientation of the piston 4 and thereby prevent leakage of liquid 7 from the outlet section 11. The supporting sealing element 13 may be made from the same material as the deformable sealing element 5 and/or the piston 4 and have the same characteristics regarding elasticity and hardness. The piston rod will preferably fill the cavity 15 when inserted in the cavity 15 to empty the injector.

In another embodiment (not shown) the piston comprises as an uppermost sealing element a second deformable sealing element as required in the invention. The lowermost deformable sealing element abuts the inner wall of the cylinder at all times after positioning in the cylinder. However, the uppermost deformable sealing element may contact the inner wall in a resting, or unloaded, position of the piston when the piston is not operated with a piston rod. Upon insertion of a piston rod into the cavity, movement of the piston towards the outlet end can create a deformation of the piston material surrounding the cavity, which deformation is directed towards the centre axis of the piston so that the uppermost deformable sealing element is "lifted" off from the inner wall. Thereby the uppermost deformable sealing element does not contribute to the static friction. However, when a piston rod is not inserted in the cavity the uppermost deformable sealing element will contribute to the static friction. Thereby a larger static friction must be overcome when attempting to refill the injector via the outlet than when using the injector via a piston rod to empty the cylinder. This makes the injector more convenient for the operator. It is preferred in this embodiment that the actuating surface of the piston is concave, e.g. with a conical shape, and that the piston rod does not fill the cavity in order for the piston rod to create the "lifting effect" and lift the uppermost deformable sealing element off the inner wall when the piston rod pushes the piston towards the outlet end.

Figure 4:
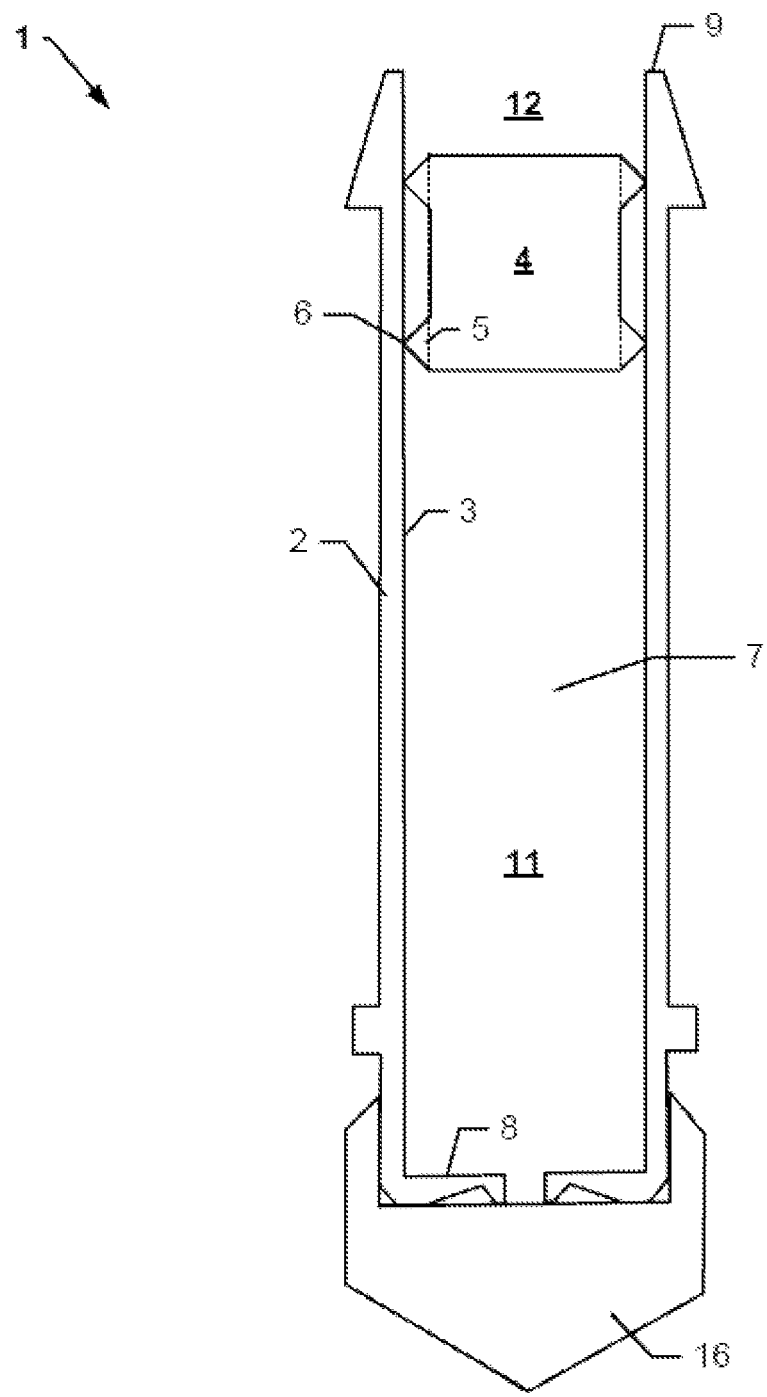
FIG. 4 shows a longitudinal cross section of an embodiment of the injector of the invention.

FIG. 4 shows an embodiment of the injector 1 according to the invention where the piston 4 is inserted in an injector prefilled with a pharmaceutical composition, for use for example with a NFI (Needle Free Injector), where by actuation means, the liquid 7 is injected through the skin under pressure and without the use of a hypodermic needle. This embodiment of the injector may also be referred to as an "ampoule".

The embodiment of FIG. 4 eliminates the need for the user to fill the injector. The injector 1 in the shown embodiment comprises a barrel cap 16 at the outlet end 8 ensuring tightness from production and until injection. The NFI shown is intended for use in a device capable of applying a sufficient force, e.g. via pressurised air or a piston rod integrated in the device, to move the piston to the outlet end with sufficient force to create a liquid stream of the pharmaceutical composition in the cylinder of the injector to penetrate the skin of a subject to deliver the pharmaceutical composition to the subject. Such devices are known to the skilled person.

The embodiment of FIG. 5a and FIG. 5b shows in cross-section, a disposable syringe representing an injector 1 of the invention. The injector 1 comprises a hypodermic needle 14 attached to an outlet 10 at the outlet end 8 of the cylinder 2 opposite the actuating end 9 of the cylinder 2. The cylinder 2 has an operating length 17 defined by the distance from the actuating end 9 of the cylinder 2 to the outlet end 8 of the cylinder 2 minus the dimension of the piston 4 parallel with the longitudinal axis. The injector 1 has a piston rod 20 having a tubular section 18 for housing the hypodermic needle 14 and an operating section 19, which tubular section 18 comprises an engagement device for engaging a complementary engagement device of the outlet 10 or the hypodermic needle 14. FIG. 5a shows the piston rod 20 mounted to house the hypodermic needle 14, and the outlet section 11 prefilled with a pharmaceutical composition. Thus, FIG. 5a represents an injector that may be supplied to the end user. The piston rod 20 mounted on the hypodermic needle 14 protects the end user from premature contact with the hypodermic needle 14. In use the piston rod 20 is removed from the hypodermic needle 14 and inserted into the actuation section 12 for the operating section 19 of the piston rod 20 to actuate the piston 4 and eject the pharmaceutical composition via the hypodermic needle 14. In the embodiment shown in FIG. 5 the piston rod 20 has a frustoconical shape and the length of the piston rod 20, i.e. the combined length of the tubular section 18 and the operating section 19 is larger than the operating length 17 of the cylinder 2. FIG. 5b shows the piston rod 20 inserted into the cylinder 2 after emptying the cylinder 2. In a preferred embodiment the piston rod 20 and the cylinder 2, e.g. at the inner wall 3 of the cylinder 2, are fitted with complementary parts of a spring-lock device (not shown) to prevent removal of the piston rod 20, and thereby reuse of the injector 1.

Figure 6:
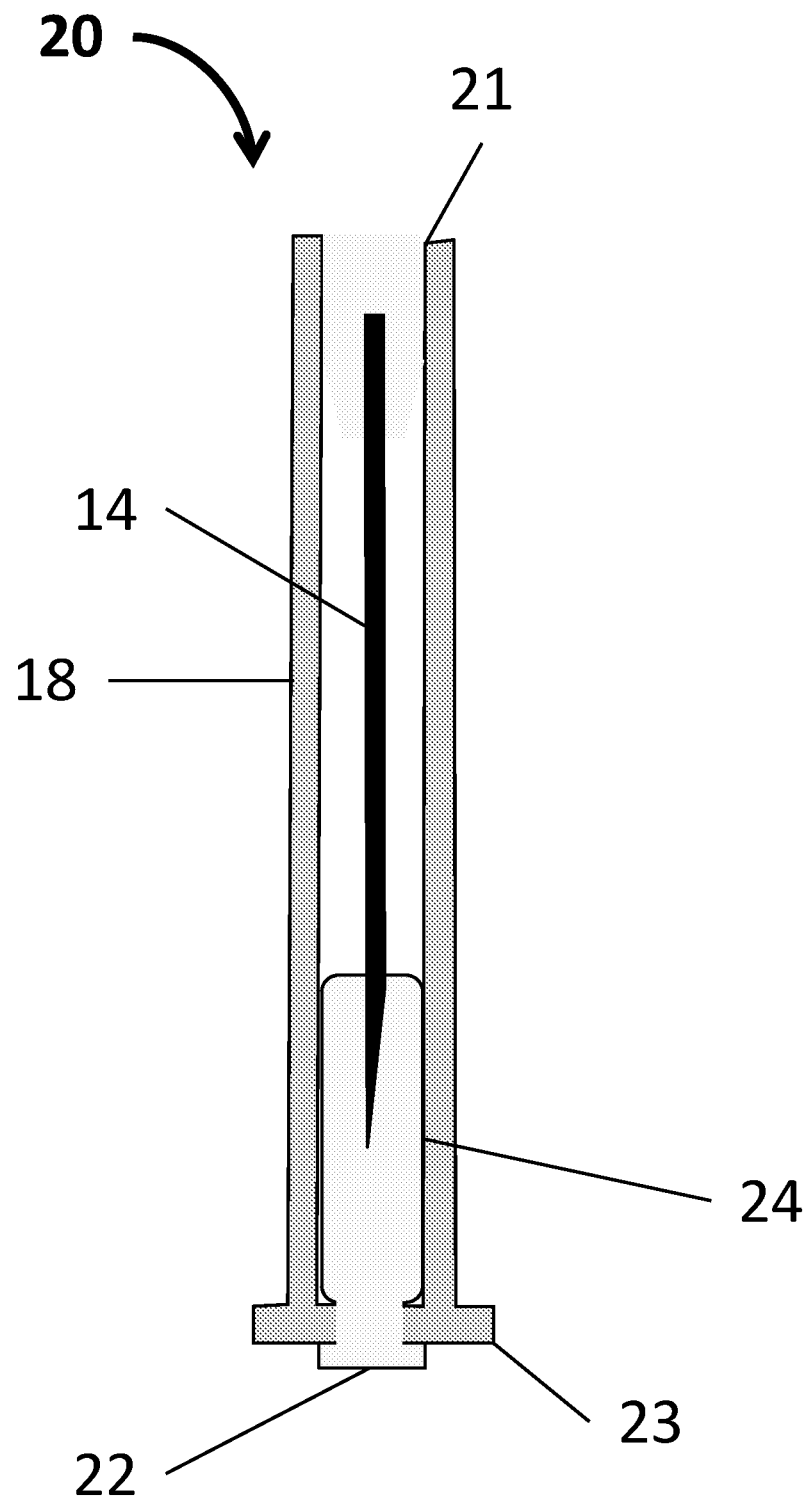
FIG. 6 shows a longitudinal cross section of an embodiment of the piston rod of the invention.

FIG. 6 illustrates a piston rod 20 of the invention with a hypodermic needle 14 inserted in the piston rod 20. The piston rod has tubular section 18, which is cylindrical, and which has a needle insertion end 21 opposite a needle protection end 22. The needle insertion end 21 comprises an engagement device for engaging the hypodermic needle 14, e.g. in the illustrated embodiment via a male-female interaction. The tip of the hypodermic needle 14 is inserted into an elastomeric material 24, thereby sealing the hypodermic needle 14. In the embodiment shown the elastomeric material 23 has been inserted via an opening at the needle protection end 22 of the tubular section 18. This embodiment allows that the elastomeric material is inserted after filling a prefilled syringe. It is also possible to insert the elastomeric material 24 via the needle insertion end 21. The piston rod 20 comprises, at the needle protection end 22, a thumb-plate 23. The thumb-plate 23 of FIG. 6 is shaped like an annular ring where the opening of the annulus allows insertion of the elastomeric material 24. In other embodiments the thumb-plate will have a disc shape without an opening. The piston rod 20 may be supplied as shown in FIG. 6, i.e. with a hypodermic needle 14 inserted into the tubular section 18 containing the elastomeric material 24. This allows that the hypodermic needle 14 is mounted on a syringe (not shown) before removing the piston rod 20 and inserting the needle insertion end 21 into the cylinder of the syringe for actuating the piston in the cylinder.

Figure 7:
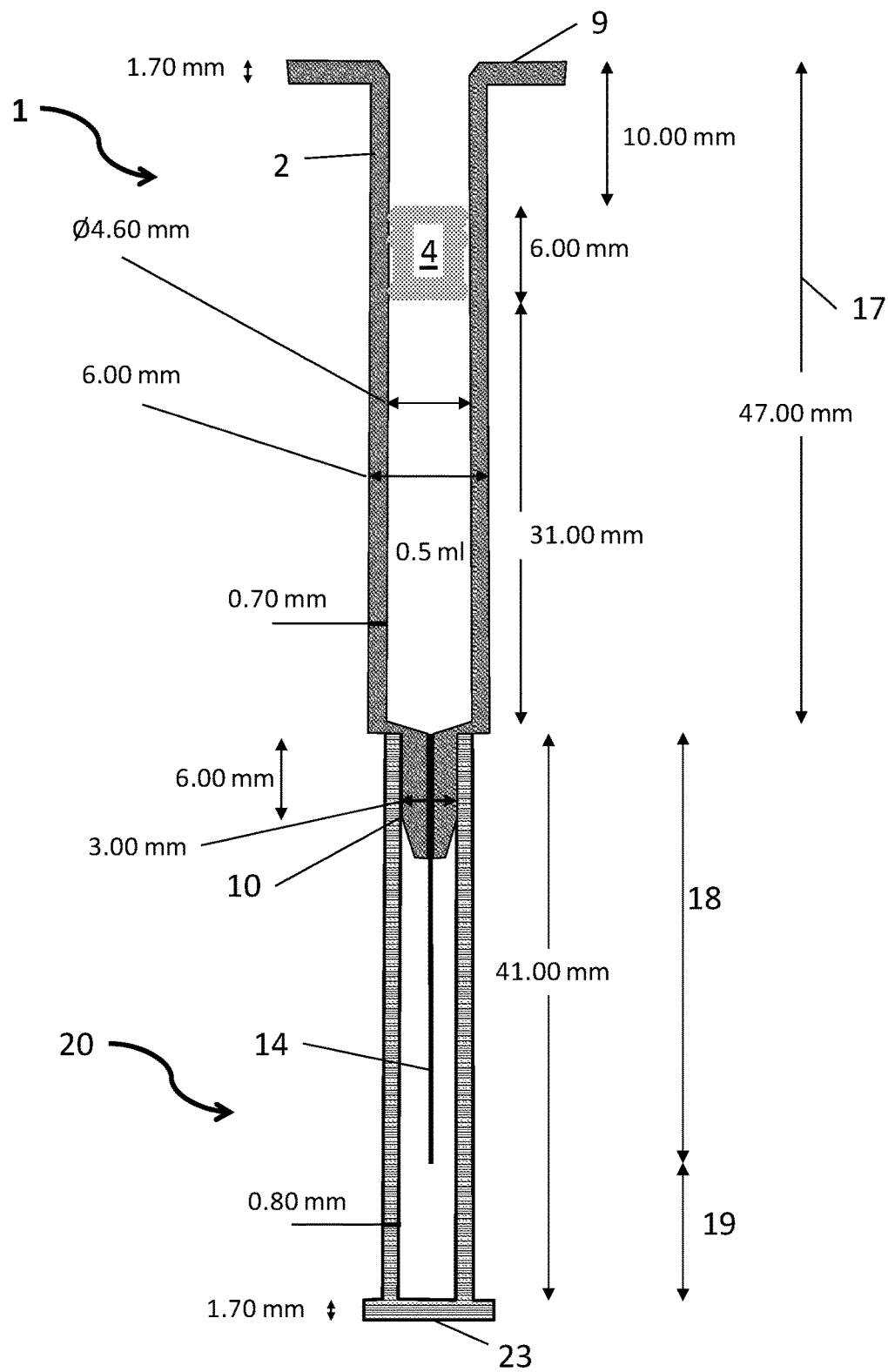
FIG. 7 shows a longitudinal cross section of an embodiment of an injector with the piston rod of the invention mounted on the syringe.
Figure 8:
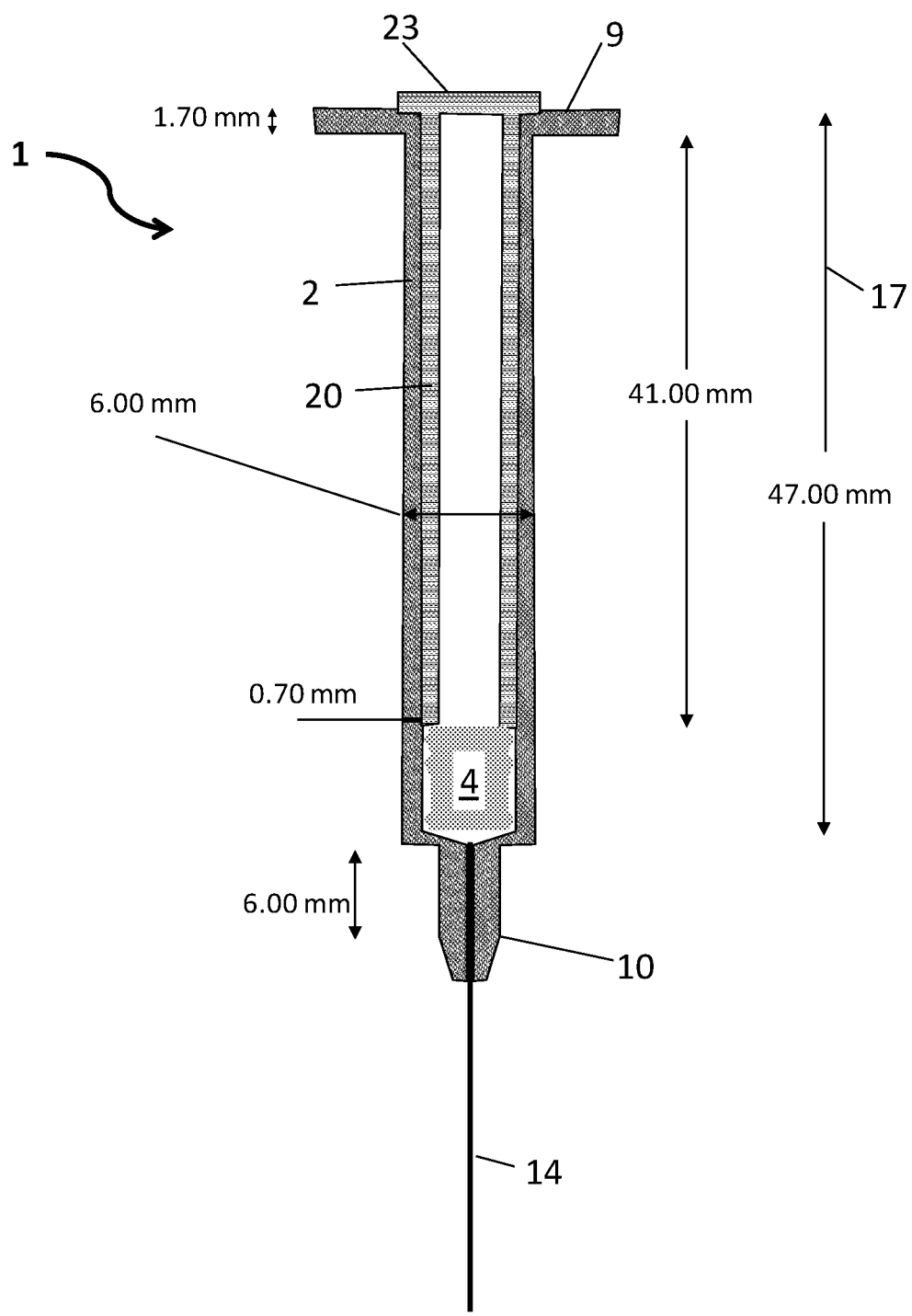
FIG. 8 shows a longitudinal cross section of an embodiment of the injector with the piston rod of the invention inserted in the syringe.

FIG. 7 and FIG. 8 show an embodiment of the piston 20 mounted on the outlet 10 of a cylinder 2 and inserted into cylinder 2, respectively. The piston rod has tubular section 18, which is cylindrical. The outer diameter of the tubular section 18 is 3.80 mm, and the inner diameter of the cylinder 2 is 4.60 mm corresponding to a ratio of 82%. This ratio stabilises axial movement of the piston rod in the cylinder. The piston rod 20 has at the needle protection end 22 a disc shaped thumb-plate 23, which increases the user comfort compared to a piston rod not having a thumb-plate.

FIG. 7 corresponds to an embodiment of the injector of the invention where the piston 4 is inserted in the cylinder 2 with a clearance of 10 mm to the actuating end 9 of the cylinder. The injector may be prefilled with a pharmaceutical composition (not shown), which may be a vaccine. The embodiment shown has a volume of 0.5 ml, e.g. when the piston 4 is inserted with a clearance of 10.00 mm, which is considered relevant for a vaccine. However, the volume, and thereby the corresponding dimensions, may be selected freely by the skilled person as appropriate for the specific purpose and pharmaceutical composition to be ejected from the injector.

FIG. 8 shows the embodiment of FIG. 7 with the piston 20 inserted fully into the cylinder 2. In FIG. 8 the operating length 17 of the cylinder 2 and the length of the tubular section are selected so that the thumb-plate 23 cannot be used to pull back the piston rod 20 once it has been inserted fully into the cylinder 2. In another embodiment (not shown) the length of the tubular section 18 is sufficient to allow that the piston rod 20 is removed from the cylinder 2. Since the piston rod 20, i.e. the device for actuating the piston, does not engage the piston 4 the piston rod 20 cannot be used to refill the syringe. The hypodermic needle 14 can instead be reinserted into the piston rod 20 so that the end user or other people will not be exposed to the tip of the hypodermic needle 14 thereby reducing risk of injury or potential exposure to contagious diseases.

The foregoing disclosure is illustrative of the present invention and is not to be construed as limiting thereof. Although one or more embodiments of the invention have been described, persons of ordinary skill in the art will readily appreciate that numerous modifications could be made without departing from the scope and spirit of the disclosed invention. As such, it should be understood that all such modifications are intended to be included within the scope of this invention. The description and the drawings illustrate one or more exemplary embodiments of the present invention and are not to be construed as limiting.

The invention claimed is:

1. An injector comprising:
    a cylinder with a longitudinal axis and an inner wall;
    a solid piston free of cavities and being inserted into the cylinder without a preset orientation, the piston having a piston body and two or more deformable sealing elements, which deformable sealing elements each abut the inner wall of the cylinder at an abutting interface and seals an annular gap between the piston body and the inner wall of the cylinder;
    a hypodermic needle attached to an outlet at an outlet end of the cylinder opposite an actuating end of the cylinder; and
    a piston rod having a tubular section for housing the hypodermic needle, the tubular section having a needle insertion end comprising an engagement device for engaging a complementary engagement device of the outlet or the hypodermic needle, and a needle protection end opposite the needle insertion end, which tubular section comprises an actuating surface to directly contact and push the piston, wherein the piston rod has a length, which is equal to or larger than an operating length of the cylinder defined by the distance from the actuating end of the cylinder to the outlet end of the cylinder minus the dimension of the piston parallel with the longitudinal axis;
    wherein the piston is free of connecting features to connect to the piston rod, and wherein the actuating surface of the piston rod is free of connecting features to connect to the piston.

2. The injector according to claim 1, wherein each deformable sealing element has a convex surface.

3. The injector according to claim 1, wherein the piston is symmetrical relative to a transverse plane.

4. The injector according to claim 1, wherein the piston has a Shore A hardness in the range of 50 to 90.

5. The injector according to claim 1, wherein the piston does not comprise any pigments or dyes.

6. The injector according to claim 1, wherein the piston rod has a thumb plate.

7. The injector according to claim 1, wherein the piston rod has an elastomeric material located so that the tip of the hypodermic needle is sealed by the elastomeric material when the hypodermic needle is inserted into the tubular section.

8. The injector according to claim 1, wherein the device for actuating the piston is at the needle insertion end.

9. The injector according to claim 1, wherein the injector is prefilled with a pharmaceutical composition.

10. The injector according to claim 1, wherein the piston body and the deformable sealing element are of the same material.

11. The injector according to claim 1, wherein the piston is made by injection moulding.

12. The injector according to claim 11, wherein the piston is made from a styrene block copolymer.

13. The injector according to claim 1, wherein the inner wall of the cylinder comprises a lubricant having a kinematic viscosity in the range of 100 cSt to 15,000 cSt.

14. The injector according to claim 1, wherein the cylinder has an inner diameter of up to 45 mm.

15. The injector according to claim 1, wherein the cylinder has an inner diameter in the range of from 2 mm to 10 mm.

16. The injector according to claim 1, wherein when the hypodermic needle is attached to the outlet of the cylinder the hypodermic needle does not project into an interior of the cylinder at the outlet end.

17. An injector comprising:
    a cylinder with a longitudinal axis and an inner wall;
    a solid piston free of cavities and being inserted into the cylinder, the piston having a piston body and two or more deformable sealing elements, which deformable sealing elements each abut the inner wall of the cylinder at an abutting interface and seals an annular gap between the piston body and the inner wall of the cylinder;
    a hypodermic needle attached to an outlet at an outlet end of the cylinder opposite an actuating end of the cylinder; and
    a piston rod having a tubular section for housing the hypodermic needle, the piston rod comprising an actuating surface to directly contact and push the piston;
    wherein the piston is free of connecting features to connect to the piston rod, and the actuating surface of the piston rod is free of connecting features to connect to the piston.

* * * * *